United States Patent
Widder et al.

(10) Patent No.: US 7,579,331 B2
(45) Date of Patent: *Aug. 25, 2009

(54) METHOD OF IMPROVED DIURESIS IN INDIVIDUALS WITH IMPAIRED RENAL FUNCTION

(75) Inventors: Kenneth J. Widder, Rancho Santa Fe, CA (US); Lauren Otsuki, San Diego, CA (US); Howard C. Dittrich, San Diego, CA (US); Scott Thomson, Poway, CA (US); Roland Blantz, Del Mar, CA (US)

(73) Assignee: Novacardia, Inc., San Diego, CA (US)

( * ) Notice: Subject to any disclaimer, the term of this patent is extended or adjusted under 35 U.S.C. 154(b) by 1009 days.

This patent is subject to a terminal disclaimer.

(21) Appl. No.: 10/830,617

(22) Filed: Apr. 23, 2004

(65) Prior Publication Data

US 2005/0004145 A1 Jan. 6, 2005

(51) Int. Cl.
*A61K 31/70* (2006.01)
(52) U.S. Cl. .......................................... 514/45
(58) Field of Classification Search .................... 514/45
See application file for complete search history.

(56) References Cited

U.S. PATENT DOCUMENTS

| | | | |
|---|---|---|---|
| 4,769,377 A | 9/1988 | Sayder et al. |
| 5,290,782 A | 3/1994 | Suzuki et al. |
| 5,395,836 A | 3/1995 | Shimada et al. |
| 5,446,046 A | 8/1995 | Belardinelli et al. |
| 5,532,368 A | 7/1996 | Kufner-Muhl et al. |
| 5,599,817 A | 2/1997 | Adamus et al. |
| 5,631,260 A | 5/1997 | Belardinelli et al. |
| 5,641,784 A | 6/1997 | Küfner-Mühl et al. |
| 5,668,139 A | 9/1997 | Belardinelli et al. |
| 5,688,802 A | 11/1997 | Kufner-Muhl et al. |
| 5,696,124 A | 12/1997 | Kufner-Muhl et al. |
| 5,736,528 A | 4/1998 | Belardinelli et al. |
| 6,187,780 B1 | 2/2001 | Blech et al. |
| 6,210,687 B1 | 4/2001 | Hosokawa et al. |
| 6,254,889 B1 | 7/2001 | Kigoshi et al. |
| 6,605,600 B1 | 8/2003 | Ensinger et al. |
| 6,649,600 B1 | 11/2003 | Kiesman et al. |
| 6,818,647 B2 | 11/2004 | Wolff et al. |
| 7,022,686 B2 | 4/2006 | Lin et al. |
| 2002/0115687 A1 | 8/2002 | Beckman et al. |
| 2002/0136775 A1 | 9/2002 | Thosar et al. |
| 2004/0229901 A1 | 11/2004 | Otsuki et al. |
| 2004/0259889 A1 | 12/2004 | Smits et al. |
| 2005/0038017 A1 | 2/2005 | Wolff et al. |
| 2005/0070524 A1 | 3/2005 | Stephenson et al. |
| 2005/0239759 A1 | 10/2005 | Otsuki et al. |
| 2005/0245546 A1 | 11/2005 | Cristalli |
| 2006/0030572 A1 | 2/2006 | Widder et al. |
| 2006/0035911 A1 | 2/2006 | Widder et al. |
| 2006/0293312 A1 | 12/2006 | Dittrich et al. |
| 2007/0238672 A1 | 10/2007 | Dittrich et al. |
| 2007/0293463 A1 | 12/2007 | Dittrich et al. |
| 2007/0293518 A1 | 12/2007 | Dittrich et al. |
| 2008/0070934 A1 | 3/2008 | Mugerditchian et al. |

FOREIGN PATENT DOCUMENTS

| | | |
|---|---|---|
| EP | 0 565 377 | 10/1993 |
| EP | 0 619 316 | 10/1994 |
| EP | 0 958 821 | 11/1999 |
| EP | 0 970 696 A1 | 1/2000 |
| JP | 1979/79296 | 6/1979 |
| JP | 1984/42383 | 3/1984 |
| WO | WO 91/10428 | 7/1991 |
| WO | WO 93/00081 | 1/1993 |
| WO | WO 94/03456 | 2/1994 |
| WO | WO 99/54331 | 10/1999 |
| WO | WO 99/55339 | 11/1999 |
| WO | WO 01/15673 | 3/2001 |
| WO | WO 01/34604 | 5/2001 |
| WO | WO 02/44182 | 6/2002 |
| WO | WO 02/49645 | 6/2002 |
| WO | WO 2004/075856 | 9/2004 |
| WO | WO 2004/096228 | 11/2004 |
| WO | WO 2007/117549 | 10/2007 |
| WO | WO 2007/149366 | 12/2007 |

OTHER PUBLICATIONS

U.S. Appl. No. 10/785,446, filed Feb. 23, 2004, Otsuki et al.

(Continued)

*Primary Examiner*—Raymond J Henley, III
(74) *Attorney, Agent, or Firm*—Richard S. Parr; Mark R. Daniel

(57) ABSTRACT

Disclosed is a pharmaceutical composition comprising a therapeutically effective amount of KW-3902, or a salt, ester, amide, metabolite, or prodrug thereof, and a non-adenosine modifying diuretic. Also disclosed are methods of inducing a diuretic effect in an animal comprising the step of administering a therapeutically effective amount of KW-3902, or a salt, ester, amide, metabolite, or prodrug thereof, in combination with second pharmaceutical composition capable of inducing a diuretic effect.

51 Claims, No Drawings

OTHER PUBLICATIONS

Aki et al.; "Effects of KW-3902, a Selective and Potent Adenosine A1 Receptor Antagonist, on Renal Hemodynamics and Urine Formation in Anesthetized Dogs," *Pharmacology*. (1997); 55:193-201.

Barrett Richard J., "Realizing the Potential of Adenosine-Receptor-Based Therapeutics," *Proc. West. Pharmacol. Soc.* (1996);39:61-66.

Belardinelli et al.; "1,3 Dipropyl-8-[2-(5,6-Epoxy)Norbornyl]Xanthine, a Potent Specific and Selective $A_1$ Adenosine Receptor Antagonist in the Guinea Pig Heart and Brain and in $DDT_1MF$-2 Cells," *Journal of Pharmacology and Experimental Theraputics*. (1995); 275(3):1167-1176.

Bertolet et al., "Differential antagonism of cardiac actions of adenosine by theophylline," *Cardiovascular Research*. (1996);32:839-845.

Broadley, Kenneth J.; "Drugs modulating adenosine receptors as potential therapeutic agents for cardiovascular diseases," *Exp. Opin. Ther. Patents*. (2000); 10(11):1669-1692.

Conlon et al.,. "Effect of Intravenous Furosemide on Serum Theophylline Concentration," *Am. J. Hosp. Pharm.* (1981);38:1345-7.

Deckert et al., "Adenosine $A_1$ receptors in human hippocampus: inhibition of [$^3$H]8-cyclopentyl-1,3-dipropylxanthine binding by antagonist drugs," *Neuroscience Letters*. (1993);150:191-194.

Daghfous et al., "Fasting in Ramadan, the asthmatics and sustained-release theophylline," Annals of Saudi Medicine. (1994).

Gellai et al., "CVT-124, a novel adenosine $A_1$ receptor antagonist with unique diuretic activity," *J. Pharmacol. Exp. Ther*. (1998);286(3):1191-6.

Giacoia et al., "Diuretics, Hypochloremia, and Outcome in Bronchopulmonary Dysplasia Patients," *Dev. Pharmacol. Ther*. (1991);4:212-220.

Gottlieb, Stephen S.; "Renal Effects of Adenosine $A_1$-Receptor Antagonists in Congestive Heart Failure," *Drugs*. (2001); 61(10):1387-1393.

Gottleib et al.; "BG9719 (CVT-124), an Adenosine $A_1$ Receptor Antagonist, Protects Against the Decline in Renal Function Observed with Diuretic Therapy," *Circulation*. (2002); 105(11):1348-1353.

Gottleib et al.; "BG9719 (CVT-124), an $A_1$-Adenosine Receptor Antagonist, Preserves Glomerular Filtration Rate and is an Active Natriuretic in Congestive Heart Failure Patients," *Circulation*. (1998); 98(17):105.

Gottlieb et al., "Effects of BG9719 (CVT-124), an $A_1$—adenosine receptor antagonist, and furosemide on glomerular filtration rate and natriuresis in patients with congestive heart failure," *J. Am. Coll. Cardiol.* (2000);35(1)56-9.

Greenberg et al.; "An Oral Adenosine Antagonist, Preserves Renal Function, Improves Sodium Excretion and is Well Tolerated in Heart Failure Patients," *AHA Meeting Orlando, Florida*. Poster/Abstract.

Ireland et al.; "FK-352 Adenosine $A_1$ Antagonist Diuretic Antihypertensive," *Drugs of the Future*. (1997); 22(4):350-352.

Jackson, Edwin K.; "A1 receptor antagonists as diuretic/natriuretic agents," *Drugs of the Future*.

Jackson et al.; "$A_1$ Receptor Blockade Induces Natriuresis with a Favorable Renal Hemodynamic Profile in SHHF/Mcc-fa(cp) Rats Chronically Treated with Salt and Furosemide," *Journal of Pharmacology and Experimental Therapeutics*.(2001); 299(3):978-987.

Kobayashi et al.; "Diuretic Effects of KW-3902 (8-(Noradamantan-3-yl)-1,3-dipropylxanthine), a Novel Adenosine $A_1$ Receptor Antagonist, in Conscious Dogs," *Biol. Pharm. Bull*. (1993); 16(12):1231-1235.

Lasser, Richad P. "The Treatment of Heart Failure in the 'Intractable' (Refractory) Phase," *Advances in Cardiopulmonary Diseases* vol. III. Banyai et al. Ed. (1966);3:296-304.

Lucas et al.; "Novel Effects of Selective Adenosine Subtype 1($A_1$) Receptor Inhibition on Renal and Pulmonary Function in Heart Failure," *Surgical Forum*. (2001); 52:95-97.

Lucas et al. "Effects of Adenosine Receptor Subtype $A_1$ on Ventricular and Renal Function," *Journal of Cardiovascular Pharmacology*. (2003); 38(4):618-624.

Lucas et al.; "Cardiorenal Effects of Adenosine Subtype 1($A_1$) Receptor Inhibition in an Experimental Model of Heart Failure," *J. American College of Surgeons*: (2002); 194(5):603-609.

Macolić et al., "Pharmacokinetics and interactions of digoxin theophylline and furosemide in diseases with edema," *International Journal of Clinical Pharmacology, Therapy and Toxicology* (1993);31(1):6-11.

Mazkereth et al., "Effects of theophylline on renal function in premature infants," *American Journal of Perinatology* (1997);14(1):45-49.

Merzon et al., "Effect of euphylline and lasix on the urea-excretion function of the kidneys in cardiac insufficiency," *Sov. Med.* (1971);34(5):119-24.

Oberbauer et al.; "Natriuretic effect of adenosine $_A$1-receptor blockade in rats," *Nephrology, Dialysis, Transplantation*. (1998);13(4):900-3.

Patterson et al.; "Selective $A_1$ Adenosine Receptor Antagonism Improves Renal Function in Heart Failure," *Circulation*. (2000); 102(18):158.

Pfister et al.; "Synthesis and Biological Evaluation of the Enantiomers of the Potent and Selective $A_1$-Adenosine Antagonist 1,3-Dipropyl-8-[2-(5,6-epoxynorbonyl)]-xanthine," *J. Med. Chem*. (1997); 40(12):1773-1778.

Pietrak A., "Intensive treatment of postoperative acute renal failure using furosemide and euphalline," *Pol. Przegl. Chir*. (1977);49(10A):1051-3.

Schnackenberg et al.; "An orally active adenosine $A_1$ receptor antagonist, FK838, increases renal excretion and maintains glomerular filtration rate in furosemide-resistant rats," *British Journal of Pharmacology*. (2003); 139(8):1383-1388.

Suzuki et al.; "Adenosine $A_1$ Antagonists. 2 Structure-Activity Relationships on Diuretic Activities and Protective Effects against Acute Renal Failure," *J. Med. Chem.* (1992); 35(16):3066-3075.

Terai et al., "General pharmacology of the new non-xanthine adenosine $A_1$ receptor antagonist (+)-(R)-[(E)-3-(2-phenylpyrazolo[1,5-a]pyridin-3-yl)acryloyl]-2-piperidine ethanol," *Arzneimittelforschung*. (1996);46(2):185-91.

Ticho et al., "Renal Effects of BG9928, an $A_1$ Adenosine Receptor Antagonist, in Rats and Nonhuman Primates," *Drug Dev. Res.* (2003);58:486-492.

Tongia et al., "Infraadditive diuretic efficacy of concurrent aminophylline and frusemide," *Indian J. Physiol. Pharmacol*. (1993);37(3):244-246.

Watson et al., "Preferences of veterinarians for drugs to treat heart disease in dogs and cats," *Aust. Vet. J.* 72:401-403.

Welch, William J.; "Adenosine type 1 receptor antagonists in fluid retaining disorders," *Expert Opin. Investig. Drugs*. (2002); 11(11)1553-1562.

Wilcox et al.; "Natriuretic and Diuretic Actions of a Highly Selective Adenosine $A_1$ Receptor Antagonist," *Journal of the American Society of Nephrology*, (1999); 10(4):714-720.

Wilcox et al.; "Adenosine $A_1$ receptor antagonists: A new class of diuretic with blockade of proximal reabsorption and tubuloglomerular feedback," *Wiener Klinische Wochenschrift*. (1997); 109(12-13):532.

Wolff et al.; "CVT-124, a Novel and Selective $A_1$-Adenosine Antagonist, is a Diuretic in Man with both Proximal and Distal Tubular Sites of Action," *Circulation*. (1996); 94(8):95.

Wolff et al.; "Renal Effects of BG9719, a Specific $A_1$ Adenosine Receptor Antagonist, in Congestive Heart Failure," *Drug Development Research*. (1998); 45:166-171.

Yao et al.; "The selective adenosine A1 receptor antagonist KW-3902 prevents radiocontrast media-induced nephropathy in rats with chronic nitric oxide deficiency," *European Journal of Pharmacology*. (2001); 414:99-104.

Yao et al., "Effect of the selective adenosine $A_1$-receptor antagonist KW-3902 on lipopolysaccharide-induced reductions in urine volume and renal blood flow in anesthetized dogs," *Jpn. J. Pharmacol*. (2000); 84(3):310-5.

Zanardo et al., "Methylxanthines Increase Renal Calcium Excretion in Preterm Infants," *Biol. Neonate*. (1995);68:169-174.

Database WPI, Section Ch, Week 199751; Derwent Publications Ltd., London GB, An 1997-550488; XP002293139 & CN 1 129105A (Zhoa M) Aug. 21, 1996 Abstract.

Dittrich, et al., Effects of the Adenosine A1 Receptor Antagonist, KW-3902, Late Breaking Trials, Heart Failure, Helsinki, Finland, Jun. 17-20, 2006.

Fingl, et al. "The Pharmacological Basis of Therapeutics" Ch. 1, p. 1 (1975).

Givertz, et al. "Effect of the Adenosine A1 Receptor Antagonist, KW-3902," Late Breaking Trials, Heart Failure 2006, Helsinki, Finland, Jun. 17-21, 2006.

Remington's Pharmaceutical Sciences, Mack Publishing Company, 18th Edition, 1990.

International Search Report for PCT/US04/012518.

Yao et al. "Diuretic Effects of KW-3902, a Novel Adenosine $A_1$—Receptor Antagonist, in Various Models of Acute Renal Failure in Rats." Jpn. J. Pharmcol. 64:281-288 (1994).

http://www.adhb.govt.nz/newborn/DrugProtocols/HydrochlorothiazidePharmacology.htm (Nov. 2001), 2 pages.

http://cpharm.vetmed.vt.edu/VM8784/CARDIOVASCULAR/fluid.htm (Jun. 4, 2000), 8 pages.

U.S. Appl. No. 12/058,532, Dittrich et al.

Anonymous "Protect-1: A study of the selective A1 Adenosine receptor antagonist KW-3902 for patients hospitalized with acute HF and volume overload to assess treatment effect on congestion and renal function", NovoCardia Study; www.clinicaltrials.gov/ct/show/NCT00328692?order=2 (May 19, 2006).

Anonymous "Study to evaluate cardiac hemodynamics and safetyof SLV320 in subjects with congestive heart failure", Solvay Pharma. www.clinicaltrials.gov/ct/show/NCT00160134?ORDER=1 (Sep. 08, 2005).

Avsar et al. "Adenosine acting via A1 receptors controls the transition to status epilepticus-like behaviour in an invitro model of epilepsy." Neuropharmacology. 47:427-437 (2004).

Bariana, D.S. "7-(1-Isoquinolinylmethyl)-theophyllines", *Can J Chem*. (1968) 46(21): 3411-13.

Beauglehole et al., "Fluorosulfonyl-substituted xanthines as selective irreversible antagonists for the A(1)-adenosine receptor" *J Med Chem*. (2000) 43(26): 4973-80.

Kaplan et al. "Effects of benzodiazepine administration on A1 adenosine receptor binding in-vivo and ex-vivo." *J Pharm. Pharmacol*. (1992); 44(8):700-703.

Massie et al., "Evolving trends in the epidemiologic factors of heart failure: rationale for preventive strategies and comprehensive disease management", *Am Heart J*., (1997) 133(6):703-12.

McOmie, J.F.W. "Protective Groups in Organic Chemistry", *Plenum Press*, London (1973).

Papesch et al.; "Synthesis of 1-Mono- and 1,3-Disubstituted 6-Aminouracils", *J Org. Chem*. (1951); 16: 1879-1890.

Rich et al.; "Cost-effectiveness analysis in clinical practice: the case of heart failure." *Arch Intern Med*. (1999) 159(15):1690-700.

Schoolwerth et al. "Renal Considerations in Angiotensin Converting Enzyme Inhibitor Therapy." Circulation. (2001); 104:1985-1991.

Treiman et al. "Treatment of seizure emergencies: Convulsive and non-convulsive status epilepticus." Epilepsy Research. (2006); 68S:S77-S82.

Wijekoon et al.; "The octant rule 21. Antioctant effects in δε-unsaturated ketones",J. Org. Chem. (1987); 52:4171-4175.

Wilkinson; "β-Blockers and Renal Function." *Drugs*. (1982) 23:195-206.

Clinical Study Report; Study HMR4902A/1001, (KW-3902 IV-EU01;RD 483/21719); 182 pages; May 18, 1999 Final.

Clinical Study Report; Study HMR4902A/1001, (KW-3902 IV-EU01;RD 483/21719); 219 pages; May 27, 2004 Final.

Apr. 10, 2009 Office Action on U.S. Appl. No. 11/454,665.

Sep. 18, 2008 Office Action on U.S. Appl. No. 11/454,665.

Mar. 21, 2008 Office Action on U.S. Appl. No. 11/454,665.

METHOD OF IMPROVED DIURESIS IN INDIVIDUALS WITH IMPAIRED RENAL FUNCTION

FIELD OF THE INVENTION

The present invention relates to the method of treatment of patients using an adenosine $A_1$ receptor antagonist in combination with other diuretics. The present invention also relates to pharmaceutical compositions containing the adenosine $A_1$ receptor antagonist in combination with other diuretics for the treatment of patients.

SUMMARY OF THE INVENTION

Disclosed is a pharmaceutical composition comprising a therapeutically effective amount of KW-3902, or a salt, ester, amide, metabolite, or prodrug thereof, and a non-adenosine modifying diuretic.

Also disclosed are methods of inducing a diuretic effect in an animal comprising the step of administering a therapeutically effective amount of KW-3902, or a salt, ester, amide, metabolite, or prodrug thereof, in combination with second pharmaceutical composition capable of inducing a diuretic effect.

DETAILED DESCRIPTION OF THE PREFERRED EMBODIMENT

Aspects of the present invention are directed to methods of treating patients using a therapeutically effective amount of KW-3902, or a salt, ester, amide, metabolite, or prodrug thereof, and a non-adenosine modifying diuretic. In another aspect, the present invention is directed to methods of improving diuresis while maintaining renal function in individuals with fluid overload using a therapeutically effective amount of KW-3902, or a salt, ester, amide, metabolite, or prodrug thereof, and a non-adenosine modifying diuretic.

The term "therapeutically effective amount" as used herein refers to that amount of a composition being administered which will relieve to some extent one or more of the signs or symptoms of the disorder being treated.

In certain embodiments, the individual being treated by the methods of the present invention suffers from renal impairment. In other embodiments, the individual does not suffer from renal impairment. These individuals include those who suffer from heart failure, such as congestive heart failure, or other maladies that result in fluid overload, without having yet disrupted normal kidney function. In some embodiments, the individual being treated by the methods of the present invention is refractory to standard diuretic therapy. In other embodiments, the individual is not refractory to standard diuretic therapy.

Thus, in another aspect, the present invention is related to methods of preventing the deterioration of renal function in individuals comprising administering a therapeutically effective amount of KW-3902, or a salt, ester, amide, metabolite, or prodrug thereof, and a non-adenosine modifying diuretic.

KW-3902 is a xanthine-derived adenosine $A_1$ receptor antagonist ($AA_1RA$). Its chemical name is 8-(3-noradamantyl)-1,3-dipropylxanthine, also known as 3,7-dihydro-1,3-dipropyl-8-(3-tricyclo[$3.3.1.0^{3,7}$]nonyl)-1H-purine-2,6-dione, and its structure is

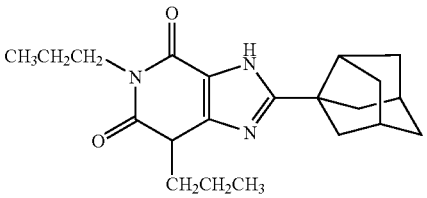

KW-3902 and related compounds useful in the practice of the present invention are described, for example, in U.S. Pat. Nos. 5,290,782, 5,395,836, 5,446,046, 5,631,260, 5,736,528, 6,210,687, and 6,254,889, the entire disclosure of all of which are hereby incorporated by reference herein, including any drawings.

A number of non-adenosine modifying diuretics are known in the art. Their examples include hydrochlorothiazides, furosemide, torsemide, bumetanide, ethacrynic acid, piretanide, norsemide, spironolactone, triamterene, metolazone and amiloridethiazides.

A significant problem encountered in treating certain conditions with individual medications is that following a course of therapy the patients become refractory to the treatment, i.e., the patients begin to respond less and less to the medication until they do not respond at all. This problem is very common in patients who suffer from, for example, congestive heart failure, and are treated with diuretics.

Individual diuretics act on a specific segment of nephrons, e.g., proximal tubule, loop of Henle, or distal tubule. One mechanism by which diuretics increase urine volume is that they inhibit reabsorption of sodium and accompanying water passing through the nephron. Thus, for example, a loop diuretic inhibits reabsorption in the loop of Henle. As a consequence, higher concentrations of sodium are passed downstream to the distal tubule. This initially results in a greater volume of urine, hence the diuretic effect. However, the distal portion of the tubule recognizes the increase in sodium concentration and the kidney reacts in two ways; one is to increase sodium reabsorption elsewhere in the nephron; the other is to feedback via adenosine $A_1$ receptors to the afferent arteriole where vasoconstriction occurs. This feedback mechanism is known as tubuloglomerular feedback (TGF). This vasoconstriction results in decreased renal blood flow and decreased glomerular filtration rate (GFR). With time, these two mechanisms result in a decrease in diuretic effect and worsening of renal function. This sequence of events contributes to the progression of disease.

The present inventors have discovered that the combination of KW-3902 with a standard diuretic is beneficial to patients who are refractory to standard therapy. KW-3902 also blocks the TGF mechanism mediated by adenosine (via $A_1$ receptors) described above. This ultimately allows for increased GFR and improved renal function, which ultimately results in more fluid passing through the loop of Henle and the distal tubule. In addition, KW-3902 inhibits the reabsorption of sodium (and, therefore, water) in the proximal tubule, which results in diuresis. Furthermore, KW-3902 is an inhibitor of TGF, which can counteract the adverse effect of some diuretics, such as proximal diuretics, which activate or promote TGF.

The combination of the invention described herein acts synergistically to further improve renal function for continued diuresis. In addition, most CHF patients are also on additional diuretics. The combination allows for greater efficacy of other more distally acting diuretics by improving renal blood flow, renal function, and in some cases, drug delivery.

Thus, in one aspect, the present invention is related to a pharmaceutical composition comprising a therapeutically effective amount of KW-3902, or a pharmaceutically acceptable salt, ester, amide, metabolite, or prodrug thereof, and a non-adenosine modifying diuretic.

In some embodiments, the non-adenosine modifying diuretic is a proximal diuretic, i.e., a diuretic that principally acts on the proximal tubule. Examples of proximal diuretics include, but are not limited to, acetazolamide, methazolamide, and dichlorphenamide. Carbonic anhydrase inhibitors are known to be diuretics that act on the proximal tubule, and are therefore, proximal diuretics. Thus, in certain embodiments, the present invention relates to the combination of KW-3902 with a carbonic anhydrase inhibitor. Combinations of KW-3902 with any proximal diuretic now known or later discovered are within the scope of the present invention.

In other embodiments, the non-adenosine modifying diuretic is a loop diuretic, i.e., a diuretic that principally acts on the loop of Henle. Examples of loop diuretics include, but are not limited to, furosemide (LASIX®), bumetanide (BUMEX®), and torsemide (TOREM®). Combinations of KW-3902 with any loop diuretic now known or later discovered are within the scope of the present invention.

In yet other embodiments, the non-adenosine modifying diuretic is a distal diuretic, i.e., a diuretic that principally acts on the distal nephron. Examples of distal diuretics include, but are not limited to, metolazone, thiazides and amiloride. Combinations of KW-3902 with any distal diuretic now known or later discovered are within the scope of the present invention.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

The term "metabolite" refers to a compound to which KW-3902 is converted within the cells of a mammal. The pharmaceutical compositions of the present invention may include a metabolite of KW-3902 instead of KW-3902. The scope of the methods of the present invention includes those instances where KW-3902 is administered to the patient, yet the metabolite is the bioactive entity.

Some of the metabolites of KW-3902 are known. These include compounds where the propyl groups on the xanthine entity are hydroxylated, or that the propyl group is an acetylmethyl ($CH_3C(O)CH_2$—) group. Other metabolites include those in which the noradamantyl group is hydroxylated (i.e., is substituted with a —OH group) or oxylated (i.e., is substituted with a =O group). Thus, examples of metabolites of KW-3902 include, but are not limited to, 8-(trans-9-hydroxy-3-tricyclo[3.3.1.0$^{3,7}$]nonyl)-1,3-dipropylxanthine (also referred to herein as "M1-trans"), 8-(cis-9-hydroxy-3-tricyclo[3.3.1.0$^{3,7}$]nonyl)-1,3-dipropylxanthine (also referred to herein as "M1-cis"), 8-(trans-9-hydroxy-3-tricyclo[3.3.1.0$^{3,7}$]nonyl)-1-(2-oxopropyl)-3-propylxanthine and 1-(2-hydroxypropyl)-8-(trans-9-hydroxy-3-tricyclo[3.3.1.0$^{3,7}$]nonyl)-3-propylxanthine.

Any amine, hydroxy, or carboxyl side chain on the metabolites, esters, or amides of the above compounds can be esterified or amidified. The procedures and specific groups to be used to achieve this end is known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In another aspect, the present invention relates to a method of inducing a diuretic effect in an animal comprising identifying a patient in need thereof and administering to the patient a therapeutically effective amount of KW-3902, or a pharmaceutically acceptable salt, ester, amide, metabolite, or prodrug thereof, in combination with a second pharmaceutical composition capable of inducing a diuretic effect. In some embodiments, the animal is refractory to standard diuretic therapy.

The methods of the present invention are effective in a patient. The patient may be an animal. The animal may be a mammal. The mammal may be selected from the group consisting of mice, rats, rabbits, guinea pigs, dogs, cats, sheep, goats, cows, primates, such as monkeys, chimpanzees, and apes, and humans. In some preferred embodiments, the animal is a human.

In some embodiments, the administering step comprises administering KW-3902 and the diuretic nearly simultaneously. These embodiments include those in which the two compounds are in the same administrable composition, i.e., a single tablet, pill, or capsule, or a single solution for intravenous injection, or a single drinkable solution, or a single dragee formulation or patch, contains both compounds. The embodiments also include those in which each compound is in a separate administrable composition, but the patient is directed to take the separate compositions nearly simultaneously, i.e., one pill is taken right after the other or that one injection of one compound is made right after the injection of another compound, etc. In some embodiments, a patient is infused with an intravenous formulation of one compound prior to the infusion of an intravenous formulation of the other compound. In these embodiments, the infusion may take some time, such as a few minutes, a half hour, or an hour, or longer. If the two intravenous infusions are done one right after the other, such administration is considered to be nearly simultaneously within the scope of the present disclosure, even though there was a lapse of some time between the start of one infusion and the start of the next infusion.

In other embodiments the administering step comprises administering one of KW-3902 and the diuretic first and then administering the other one of KW-3902 and the diuretic. In these embodiments, the patient may be administered a composition comprising one of the compounds and then at some time, a few minutes or a few hours, later be administered another composition comprising the other one of the compounds. Also included in these embodiments are those in which the patient is administered a composition comprising one of the compounds on a routine or continuous basis while receiving a composition comprising the other compound occasionally. In further embodiments, the patient may receive both compounds on a routine or continuous basis, such a continuous infusion of the compound through an IV line.

In some embodiments, KW-3902 is administered in a dose of 2.5 mg, 5 mg, 10 mg, 15 mg, 30 mg, 60 mg, or 100 mg, or higher. In some embodiments, the administered KW-3902 is in an injectable form, while in other embodiments, the administered KW-3902 is in a solid formulation.

In another aspect, the present invention relates to a method of maintaining or restoring the diuretic effect of a non-adenosine modifying diuretic in a patient comprising identifying a patient in need thereof, and administering to the patient a therapeutically effective amount of KW-3902, or a pharmaceutically acceptable salt, ester, amide, metabolite, or prodrug thereof, in combination with said non-adenosine modifying diuretic.

In certain embodiments, the diuretic used in the methods of the present invention is furosemide. In some embodiments, furosemide is administered in a dose of 20 mg, 40 mg, 60 mg, 80 mg, 100 mg, 120 mg, 140 mg, or 160 mg, or higher. The administration may be oral or intravenous. When furosemide is administered intravenous, it may be administered as a single injection or as a continuous infusion. When the administration is through a continuous infusion, the dosage of furosemide may be less than 1 mg per hour, 1 mg per hour, 3 mg per hour, 5 mg per hour, 10 mg per hour, 15 mg per hour, 20 mg per hour, 40 mg per hour, 60 mg per hour, 80 mg per hour, 100 mg per hour, 120 mg per hour, 140 mg per hour, or 160 mg per hour, or higher.

In yet another aspect, the present invention relates to a method of maintaining or restoring renal function in a patient comprising identifying a patient in need thereof, and administering a therapeutically effective amount of KW-3902, or a pharmaceutically acceptable salt, ester, amide, metabolite, or prodrug thereof, in combination with second pharmaceutical composition capable of inducing a diuretic effect.

In the context of the present disclosure, by "maintaining" renal function it is meant that the renal function, as measured by creatinine clearance rate, remains unchanged for a period of time after the start of the therapy. In other words, by "maintaining" renal function it is meant that the rate of renal impairment, i.e., the rate of decrease in the creatinine clearance rate, is slowed or arrested for a period of time, however brief that period may be. By "restoring" renal function it is meant that the renal function, as measured by creatinine clearance rate, has improved, i.e., has become higher, after the start of the therapy.

In certain embodiments, the second pharmaceutical composition comprises a loop diuretic and a distal diuretic.

In a further aspect, the present invention relates to a method of treating a patient with a pharmaceutical composition as described herein. In some embodiments, the patient is refractory to standard diuretic therapy.

Certain patients who suffer from a cardiac condition, such as congestive heart failure, later develop renal impairment. The present inventors have discovered that if a patient presented with a cardiac condition, and little to no renal impairment, is treated with a pharmaceutical composition as described herein, the onset of renal impairment is delayed or arrested, compared to a patient who receives standard treatment. Thus, aspects of the present invention relate to a method of preventing the deterioration of renal function, delaying the onset of renal impairment, or arresting the progress of renal impairment in a patient comprising identifying a patient in need thereof, and administering a therapeutically effective amount of KW-3902, or a salt, ester, amide, metabolite, or prodrug thereof, and a non-adenosine modifying diuretic.

The term "treating" or "treatment" does not necessarily mean total cure. Any alleviation of any undesired signs or symptoms of the disease to any extent or the slowing down of the progress of the disease can be considered treatment. Furthermore, treatment may include acts that may worsen the patient's overall feeling of well being or appearance. Treatment may also include lengthening the life of the patient, even if the symptoms are not alleviated, the disease conditions are not ameliorated, or the patient's overall feeling of well being is not improved. Thus, in the context of the present invention, increasing the urine output volume, decreasing the level of serum creatinine, or increasing creatinine clearance, may be considered treatment, even if the patient is not cured or does not generally feel better.

In another aspect, the present invention relates to a method of treating a patient suffering from CHF comprising identifying a patient in need thereof, and administering to said patient a therapeutically effective amount of KW-3902, or a pharmaceutically acceptable salt, ester, amide, metabolite, or prodrug thereof, in combination with second pharmaceutical composition capable of inducing a diuretic effect.

In a further aspect, the present invention relates to a method of improving overall health outcomes, decreasing morbidity rates, or decreasing mortality rates in patients comprising identifying a patient in need thereof, and administering to said patient a therapeutically effective amount of KW-3902, or a pharmaceutically acceptable salt, ester, amide, metabolite, or prodrug thereof, in combination with second pharmaceutical composition capable of inducing a diuretic effect.

Overall health outcomes are determined by various means in the art. For example, improvements in morbidity and/or mortality rates, improvements in the patient's general feelings, improvements in the quality of life, improvements in the level of comfort at the end of life, and the like, are considered when overall health outcome are determined. Mortality rate is the number of patients who die while undergoing a particular treatment for a period of time compared to the overall number of patients undergoing the same or similar treatment over the same period of time. Morbidity rates are determined using various criteria, such as the frequency of hospital stays, the length of hospital stays, the frequency of visits to the doctor's office, the dosage of the medication being administered, and the like.

In some embodiments, the patient whose overall health outcome, morbidity and/or mortality rate is being improved suffers from CHF. In other embodiments, the patient suffers from renal impairment.

Other $AA_1RAs$ are known in the art, for example, BG 9719, described in U.S. Patent Application Publication No. 2002/0115687 A1. BG 9719 is also a xanthine-derivative compound, whose structure bears some similarity to that of KW-3902. However, the present inventors have surprisingly discovered that despite the structural similarity of these compounds, they behave remarkably differently in various ways. For example, solid formulations of KW-3902 are easily obtained, and in fact disclosed in U.S. Pat. No. 6,254,889. These formulations are found to be very stable at room temperature for over 3 years. Pharmacokinetic data from single administration in normal volunteers of both IV and oral dosage forms of KW-3902 show a bioavailability of ~25% for the oral dosage form and demonstrate its diuretic effect. The 20 mg oral dose group showed a 2× increase in urine volume compared to the placebo group at over the first two hours after treatment. (Unpublished clinical study data.) By contrast, literature references show that BG 9719 cannot be formulated in a solid form. For example, it has been reported that the development program for BG 9719 has "been hampered by its poor solubility as well as the lack of a suitable oral formulation" (B. Ticho et al, Drug Development Research 58:486-492 (2003)).

The two compounds also show significantly different affinity for adenosine $A_1$ receptors and are not equally selective for adenosine $A_1$ receptors over adenosine $A_{2a}$ receptors. The data for the two compounds are shown in the table below.

| Compound | $A_1K_I$ (nM) | $A_{2a}K_I$ (nM) |
| --- | --- | --- |
| BG 9719 | 0.45 ± .04 | 1100 ± 318 |
| KW 3902 | 0.72 ± .12 | 108 ± 15 |

These data show BG 9719 to have a 60% great affinity for the $A_1$ receptor than KW-3902. Selectivity for the $A_1$ receptor over the $A_{2a}$ receptor by BG 9719 is 16 times greater than selectivity by KW-3902. The data for BG 9719 were obtained from the U.S. Patent Application Publication No. 2002/0115687 A1, while the data for KW-3902 were published in Pfister, J. R, et al, *J. Med. Chem.* 1997, 40, 1773-1778.

Furthermore, at equi-potent dosages of KW-3902 and BG 9719 (unpublished clinical study data; Wolff et al, Drug Development Research 45:166-177 (1998)), when compared to placebo, KW-3902 shows significantly greater diuretic effect than BG 9719. For the purposes of the analysis below, the equi-potent dose of KW 3902 was calculated by multiplying the ratio of the $A_1K_1$ by the dose of BG 9719 i.e. (0.72/0.45)×0.3 mg/kg=0.48 mg/kg.

| Compound | $A_1K_I$ (nM) | Equi-potent Dose | % Urine volume increase over placebo, 3 hr |
| --- | --- | --- | --- |
| BG 9719 | 0.45 ± .04 | .3 mg/kg or 20 mg | 33% |
| KW-3902 | 0.72 ± .12 | .48 mg/kg or 30 mg | 195% |

These data collectively show that while BG 9719 and KW-3902 have some structural similarity, their pharmacokinetic activity and physiological function is quite surprisingly different, with KW-3902 providing an unexpected advantage over BG 9719.

Methods of the present invention described herein may be practiced by using, instead of KW-3902, a xanthine-derivative compound of Formula I or a pharmaceutically acceptable salt thereof,

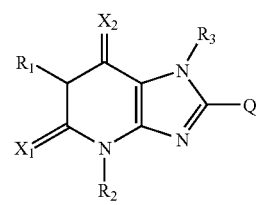

(I)

where
each of $X_1$ and $X_2$ independently represents oxygen or sulfur;
Q represents:

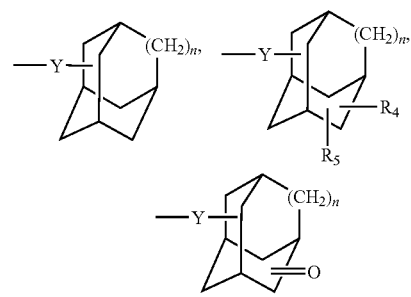

or where Y represents a single bond or alkylene having 1 to 4 carbon atoms, n represents 0 or 1;
each of $R_1$ and $R_2$ independently represents hydrogen, lower alkyl, allyl, propargyl, or hydroxy-substituted, oxo-substituted or unsubstituted lower alkyl, and $R_3$ represents hydrogen or lower alkyl, or
$R_4$ and $R_5$ are the same or different and each represent hydrogen or hydroxy, and when both $R_4$ and $R_5$ are hydrogen, at least one of $R_1$ and $R_2$ is hydroxy-substituted or oxo-substituted lower alkyl, provided that when Q is

then $R_1$, $R_2$ and $R_3$ are not simultaneously methyl.

In some embodiments, both of $R_1$ and $R_2$ of the compound of Formula I are lower alkyl and $R_3$ is hydrogen; and both of $X_1$ and $X_2$ are oxygen. In other embodiments, $R_1$, $R_2$ and $R_3$ independently represents hydrogen or lower alkyl. In still other embodiments, each of $R_1$ and $R_2$ independently represents allyl or propargyl and $R_3$ represents hydrogen or lower alkyl. In certain embodiments, $X_1$ and $X_2$ are both oxygen and n is 0.

In some embodiments, $R_1$ is hydroxy-substituted, oxo-substituted or unsubstituted propyl; $R_2$ is hydroxy-substituted or unsubstituted propyl; and Y is a single bond. In other embodiments, $R_1$ is propyl, 2-hydroxypropyl, 2-oxopropyl or 3-oxopropyl; $R_2$ is propyl, 2-hydroxypropyl or 3-hydroxypropyl.

In some embodiments Q is

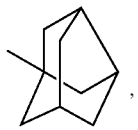

while in other embodiments Q is

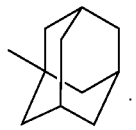

In other embodiments, Q is 9-hydroxy, 9-oxo or 6-hydroxy substituted 3tricyclo[3.3.1.0$^{3,7}$]nonyl, or 3-hydroxy-1tricyclo[3.3.1.1$^{3,7}$]decyl.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabeleting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Some emulsions used in solubilizing and delivering the xanthine derivatives described above are discussed in U.S. Pat. No. 6,210,687, which is incorporated by reference herein in its entirety, including any drawings.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.01 to 1000 mg/kg of the patient's body weight. The dosage may be a single one or a series of two or more given in the course of one or more days, as is needed by the patient.

The daily dosage regimen of KW-3902 for an adult human patient may be, for example, an oral dose of between 0.1 mg and 500 mg, preferably between 1 mg and 250 mg, e.g. 5 to 200 mg or an intravenous, subcutaneous, or intramuscular dose of between 0.01 mg and 500 mg, preferably between 0.1 mg and 200 mg, e.g. 1 to 100 mg of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more, or for months or years.

In certain aspects, KW-3902 is administered in conjunction with a diuretic. In these aspects, the dose of the diuretic is that which constitutes standard diuretic therapy. Those of skill in the art know what dosage of diuretics to administer to a patient in need thereof. However, because of the diuretic effect of KW-3902, the need for higher doses of the diuretic are eliminated when KW-3902 is administered to a patient in conjunction with the diuretic.

Dosage amount and interval may be adjusted individually to provide plasma levels of the active moiety that are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

Treatment of Individuals with Fluid Overload and Renal Impairment

A patient with fluid overload, as manifested by peripheral edema, dyspnea, and/or other signs or symptoms presents to the hospital, clinic, or doctor's office. The patient also shows some degree of renal impairment. In addition to standard of care therapy which would include IV diuretics e.g. IV furosemide, bumetanide and/or oral metolazone, the patient is also given 2.5 mg of KW-3902 in injectable form. The patient is administered 2.5 mg of KW-3902 and 40 mg of furosemide at 24 hour intervals or more frequently as needed. The patient's fluid intake and output, urine volume, serum and urine creatinine levels, electrolytes and cardiac function are monitored.

At the discretion of the attending physician, the dosage of KW-3902 can be increased to 15 mg, 30 mg, or 60 mg either during the treatment or as the initial dose. In addition, the dosage of furosemide can be increased to 60 mg, 80 mg, 100 mg, 120 mg, 140 mg, or 160 mg either during the treatment or as the initial dose, or furosemide can be given as a continuous infusion.

Example 2

Treatment of Individuals Refractory to Standard IV Diuretic Therapy

A hospitalized patient who has been treated with maximum amounts of IV diuretic and is still symptomatic, fluid overloaded, or whose urine output is less than fluid intake is evaluated for further treatment. A 10 mg dose of KW-3902 in injectable form is infused through the IV line. The patient receives continued treatment with furosemide, and also receives 10 mg of KW-3902 at 6 hour intervals, or more or less frequently as needed. The patient's fluid intake and output, urine volume, serum and urine creatinine levels, electrolytes and cardiac function are monitored.

At the discretion of the attending physician, the dosage of KW-3902 can be increased to 15 mg, 30 mg, 60 mg, or 100 mg either during the treatment or as the initial dose, or furosemide can be given as a continuous infusion.

Example 3

Treatment of Individuals with Fluid Overload

A patient with fluid overload, as manifested by peripheral edema, dyspnea, and/or other signs or symptoms presents to the hospital, clinic, or doctor's office. In addition to standard of care therapy which would include IV diuretics e.g. IV furosemide, bumetanide and/or oral metolazone, the patient is also given 2.5 mg of KW-3902 in injectable form. The patient is administered 2.5 mg of KW-3902 and 40 mg of furosemide at 24 hour intervals, or furosemide can be given as a continuous infusion. The patient's fluid intake and output, urine volume, serum and urine creatinine levels, electrolytes and cardiac function are monitored.

At the discretion of the attending physician, the dosage of KW-3902 can be increased to 15 mg, 30 mg, or 60 mg either during the treatment or as the initial dose. In addition, the dosage of furosemide can be increased to 60 mg, 80 mg, 100 mg, 120 mg, 140 mg, or 160 mg either during the treatment or as the initial dose. This treatment can be used for patients whether or not they suffer from renal impairment.

Example 4

Treatment of Individuals with Fluid Overload and Impaired Renal Function

A patient with fluid overload, as manifested by peripheral edema, dyspnea, and/or other signs or symptoms presents himself to the physician's office or clinic. The patient has been on a therapy regimen that includes oral diuretics and, in addition, to needing a higher dose of diuretics to manage his/her fluid balance, the patient is now showing impaired renal function. The patient is prescribed 5 mg of KW-3902 to be taken orally, once daily, concurrent with other diuretic therapy. The patient's fluid intake and output, urine volume, serum and urine creatinine levels, electrolytes and cardiac function are monitored.

At the discretion of the attending physician, the dosage of KW-3902 can be increased to 15 mg, 30 mg, 60 mg, 80 mg, or 100 mg oral either during the treatment or as the initial dose. In addition, the dosage of furosemide can be increased to 60 mg, 80 mg, 100 mg, 120 mg, 140 mg, or 160 mg either during the treatment or as the initial dose.

Example 5

Treatment of Individuals with Fluid Overload

A patient with fluid overload, as manifested by peripheral edema, dyspnea, and/or other signs or symptoms presents to the physician's office or clinic. The patient has been on a therapy regimen that includes oral diuretics and needs a higher dose of diuretics to manage his/her fluid balance. To delay or prevent the onset of renal impairment and/or to delay the need to use higher dosages of standard diuretics, the patient is prescribed 5 mg of KW-3902 to be taken orally, once daily, concurrent with their diuretic therapy. The patient's fluid intake and output, urine volume, serum and urine creatinine levels, electrolytes and cardiac function are monitored.

At the discretion of the attending physician, the dosage of KW-3902 can be increased to 15 mg, 30 mg, 60 mg, 80 mg, or 100 mg oral either during the treatment or as the initial dose. In addition, the dosage of furosemide can be increased to 60 mg, 80 mg, 100 mg, 120 mg, 140 mg, or 160 mg either during the treatment or as the initial dose.

Example 6

Treatment of Individuals with Congestive Heart Failure

A patient with congestive heart failure presents to the physician's office or clinic. The patient is put on a therapy regimen that includes oral diuretics to manage his/her fluid balance. To delay or prevent the onset of renal impairment and/or to delay the need to use higher dosages of standard diuretics, the patient is also prescribed 5 mg of KW-3902 to be taken orally, once daily, concurrent with their diuretic therapy. The patient's fluid levels, urine volume, serum and urine creatinine levels, electrolytes and cardiac function are monitored.

At the discretion of the attending physician, the dosage of KW-3902 can be increased to 15 mg, 30 mg, 60 mg, 80 mg, or 100 mg oral either during the treatment or as the initial dose. In addition, the dosage of furosemide can be increased to 60 mg, 80 mg, 100 mg, 120 mg, 140 mg, or 160 mg either during the treatment or as the initial dose.

Example 7

Improving Health Outcomes for of Individuals with Congestive Heart Failure

A patient with congestive heart failure presents to the physician's office or clinic. The patient is put on a therapy regimen that includes oral diuretics to manage his/her fluid balance. To improve overall health outcomes (i.e., morbidity or mortality rates due to CHF), the patient is also prescribed 5 mg of KW-3902 to be taken orally, once daily, concurrent with their diuretic therapy, or similar doses of KW-3902 is administered to the patient intravenously. The patient's fluid levels, urine volume, serum and urine creatinine levels, electrolytes and cardiac function are monitored.

At the discretion of the attending physician, the dosage of KW-3902 can be increased to 15 mg, 30 mg, 60 mg, 80 mg, or 100 mg either during the treatment or as the initial dose. In addition, the dosage of furosemide can be increased to 60 mg, 80 mg, 100 mg, 120 mg, 140 mg, or 160 mg either during the treatment or as the initial dose.

What is claimed is:

1. A method for improving renal function, comprising:
   identifying a human patient suffering from impaired creatinine clearance; and
   intravenously administering to the patient 30 mg of KW-3902, or a pharmaceutically acceptable salt, ester, amide, metabolite, or prodrug thereof, effective to maintain or increase creatinine clearance, in conjunction with a non adenosine-modifying diuretic.

2. The method of claim 1, wherein the non adenosine-modifying diuretic is a proximal diuretic.

3. The method of claim 1, wherein the non adenosine-modifying diuretic is a loop diuretic.

4. The method of claim 1, wherein the non adenosine-modifying diuretic is a distal diuretic.

5. A method for maintaining renal function, comprising:
   identifying a human patient having impaired creatinine clearance; and
   intravenously administering to the patient 30 mg of KW-3902, or a pharmaceutically acceptable salt, ester, amide, metabolite, or prodrug thereof, in conjunction with a non adenosine-modifying diuretic;
   thereby the rate of impairment in creatinine clearance is slowed or arrested for a period of time.

6. The method of claim 5, wherein the non adenosine-modifying diuretic is a proximal diuretic.

7. The method of claim 5, wherein the non adenosine-modifying diuretic is a loop diuretic.

8. The method of claim 5, wherein the non adenosine-modifying diuretic is a distal diuretic.

9. The method of claim 5, wherein said 30 mg of KW-3902 is effective to maintain creatinine clearance.

10. A method for restoring renal function, comprising:
    identifying a human patient having impaired creatinine clearance; and
    intravenously administering to the patient 30 mg of KW-3902, or a pharmaceutically acceptable salt, ester, amide, metabolite, or prodrug thereof, in conjunction with a non adenosine-modifying diuretic;
    thereby the creatinine clearance becomes higher.

11. The method of claim 10, wherein said 30 mg of KW-3902 is effective to increase creatinine clearance.

12. The method of claim 10, wherein the non adenosine-modifying diuretic is a proximal diuretic.

13. The method of claim 10, wherein the non adenosine-modifying diuretic is a loop diuretic.

14. The method of claim 10, wherein the non adenosine-modifying diuretic is a distal diuretic.

15. A method for improving renal function, comprising:
    identifying a human patient suffering from increased serum creatinine levels; and
    intravenously administering to the patient 30 mg of KW-3902, or a pharmaceutically acceptable salt, ester, amide, metabolite, or prodrug thereof, effective to maintain or decrease serum creatinine levels, in conjunction with a non adenosine-modifying diuretic.

16. The method of claim 15, wherein the non adenosine-modifying diuretic is a proximal diuretic.

17. The method of claim 15, wherein the non adenosine-modifying diuretic is a loop diuretic.

18. The method of claim 15, wherein the non adenosine modifying diuretic is a distal diuretic.

19. A method for maintaining renal function, comprising:
identifying a human patient in need thereof having increased serum creatinine levels; and
intravenously administering to the patient 30 mg of KW-3902, or a pharmaceutically acceptable salt, ester, amide, metabolite, or prodrug thereof, in conjunction with a non adenosine-modifying diuretic;
thereby the rate of increase in serum creatinine level is slowed or arrested for a period of time.

20. The method of claim 19, wherein said 30mg of KW-3902 is effective to maintain creatinine clearance.

21. The method of claim 19, wherein the non adenosine-modifying diuretic is a proximal diuretic.

22. The method of claim 19, wherein the non adenosine-modifying diuretic is a loop diuretic.

23. The method of claim 19, wherein the diuretic is a non adenosine-modifying distal diuretic.

24. A method for restoring renal function, comprising:
identifying a human patient in need thereof having increased serum creatinine levels; and
intravenously administering to the patient 30 mg of KW-3902, or a pharmaceutically acceptable salt, ester, amide, metabolite, or prodrug thereof, in conjunction with a non adenosine-modifying diuretic;
thereby decreasing serum creatinine levels.

25. The method of claim 24, wherein said 30 mg of KW-3902 is effective to increase creatinine clearance.

26. The method of claim 24, wherein the non adenosine-modifying diuretic is a proximal diuretic.

27. The method of claim 24, wherein the non adenosine-modifying diuretic is a loop diuretic.

28. The method of claim 24, wherein the non adenosine-modifying diuretic is a distal diuretic.

29. A method for improving renal function, comprising:
identifying a human patient suffering from congestive heart failure and renal impairment; and
intravenously administering to the patient 30 mg of KW-3902, or a pharmaceutically acceptable salt, ester, amide, metabolite, or prodrug thereof, effective to maintain or decrease serum creatinine levels, in conjunction with a non adenosine-modifying diuretic.

30. The method of claim 29, wherein the non adenosine-modifying diuretic is a proximal diuretic.

31. The method of claim 29, wherein the non adenosine-modifying diuretic is a loop diuretic.

32. The method of claim 29, wherein the non adenosine-modifying diuretic is a distal diuretic.

33. A method for maintaining renal function, comprising:
identifying a human patient suffering from congestive heart failure and renal impairment; and
intravenously administering to the patient 30 mg of KW-3902, or a pharmaceutically acceptable salt, ester, amide, metabolite, or prodrug thereof, in conjunction with a non adenosine-modifying diuretic;
thereby slowing or arresting rate of increase in serum creatinine level for a period of time.

34. The method of claim 33, wherein said 30 mg of KW-3902 is effective to maintain creatinine clearance.

35. The method of claim 33, wherein the non adenosine-modifying diuretic is a proximal diuretic.

36. The method of claim 33, wherein the non adenosine-modifying diuretic is a loop diuretic.

37. The method of claim 33, wherein the non adenosine-modifying diuretic is a distal diuretic.

38. A method for restoring renal function, comprising:
identifying a human patient suffering from congestive heart failure and renal impairment; and
intravenously administering to the patient 30 mg of KW-3902, or a pharmaceutically acceptable salt, ester, amide, metabolite, or prodrug thereof, in conjunction with a non adenosine-modifying diuretic;
thereby decreasing serum creatinine levels.

39. The method of claim 38, wherein said 30 mg of KW-3902 is effective to increase creatinine clearance.

40. The method of claim 38, wherein the non adenosine-modifying diuretic is a proximal diuretic.

41. The method of claim 38, wherein the non adenosine-modifying diuretic is a loop diuretic.

42. The method of claim 38, wherein the non adenosine-modifying diuretic is a distal diuretic.

43. The method of claim 3, wherein said loop diuretic is furosemide.

44. The method of claim 7, wherein said loop diuretic is furosemide.

45. The method of claim 13, wherein said loop diuretic is furosemide.

46. The method of claim 17, wherein said loop diuretic is furosemide.

47. The method of claim 22, wherein said loop diuretic is furosemide.

48. The method of claim 27, wherein said loop diuretic is furosemide.

49. The method of claim 31, wherein said loop diuretic is furosemide.

50. The method of claim 36, wherein said loop diuretic is furosemide.

51. The method of claim 41, wherein said loop diuretic is furosemide.

* * * * *